(12) United States Patent
Lachmanovich et al.

(10) Patent No.: US 10,460,441 B2
(45) Date of Patent: *Oct. 29, 2019

(54) TRACHEA MARKING

(71) Applicant: COVIDIEN LP, Mansfield, MA (US)

(72) Inventors: Elad D. Lachmanovich, Modiin (IL); Evgeni Kopel, Barkan (IL); Eyal Klein, Tel Aviv (IL)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/112,105

(22) Filed: Aug. 24, 2018

(65) Prior Publication Data

US 2018/0365832 A1   Dec. 20, 2018

Related U.S. Application Data

(63) Continuation of application No. 15/682,893, filed on Aug. 22, 2017, now Pat. No. 10,062,166, which is a
(Continued)

(51) Int. Cl.
*G06T 15/00* (2011.01)
*G06T 7/00* (2017.01)
(Continued)

(52) U.S. Cl.
CPC .......... *G06T 7/0012* (2013.01); *A61B 5/0033* (2013.01); *G06F 3/04815* (2013.01);
(Continued)

(58) Field of Classification Search
None
See application file for complete search history.

(56) References Cited

U.S. PATENT DOCUMENTS

| 5,592,939 A | 1/1997 | Martinelli |
| 5,611,025 A | 3/1997 | Lorensen et al. |

(Continued)

FOREIGN PATENT DOCUMENTS

| JP | 2009539540 A | 11/2009 |
| JP | 2012096024 A | 5/2012 |

OTHER PUBLICATIONS

Seijo et al., "Preliminary Experience with the Use of Electromagnetic Navigation for the Diagnosis of Peripheral Pulmonary Nodules and Enlarged Mediastinal Lymph Nodes", Archivos De Bronconeumologia, Ediciones Doyma S.A., Barcelona, ES, vol. 43, No. 8, Jan. 2007, pp. 46-463 (Year: 2007).*
(Continued)

*Primary Examiner* — Martin Mushambo

(57) ABSTRACT

Disclosed are systems, devices, and methods for marking a main carina and a trachea of a patient, an exemplary method comprising importing slice images of a chest of the patient, generating a three-dimensional (3D) model based on the imported slice images, displaying the 3D model in a graphical user interface (GUI), locating the main carina by viewing 2D images of the 3D model in an axial orientation, marking the main carina in one of the 2D images of the 3D model, adjusting a view plane of the 3D model around a rotation axis defined by the marked location of the main carina to adjust the view plane from an axial orientation to a coronal orientation while keeping the main carina in the view plane to thereby display the entire trachea on the GUI, and marking an upper end of the trachea in one of the 2D images of the 3D model.

12 Claims, 5 Drawing Sheets

Related U.S. Application Data continuation of application No. 14/753,674, filed on Jun. 29, 2015, now Pat. No. 9,754,367.

(60) Provisional application No. 62/020,253, filed on Jul. 2, 2014.

(51) Int. Cl.
*G06F 3/0481* (2013.01)
*G06T 17/00* (2006.01)
*G06T 19/00* (2011.01)
*A61B 5/00* (2006.01)

(52) U.S. Cl.
CPC .............. *G06T 17/00* (2013.01); *G06T 19/00* (2013.01); *G06T 2200/24* (2013.01); *G06T 2210/41* (2013.01); *G06T 2219/008* (2013.01)

(56) References Cited

U.S. PATENT DOCUMENTS

| | | | |
|---|---|---|---|
| 5,676,673 A | 10/1997 | Ferre et al. | |
| 5,697,377 A | 12/1997 | Wittkampf | |
| 5,699,799 A | 12/1997 | Xu et al. | |
| 5,715,836 A | 2/1998 | Kliegis et al. | |
| 5,729,129 A | 3/1998 | Acker | |
| 5,752,513 A | 5/1998 | Acker et al. | |
| 5,782,762 A | 7/1998 | Vining | |
| 5,881,124 A | 3/1999 | Giger et al. | |
| 5,891,030 A | 4/1999 | Johnson et al. | |
| 5,913,820 A | 6/1999 | Bladen et al. | |
| 5,920,319 A | 7/1999 | Vining et al. | |
| 5,967,980 A | 10/1999 | Ferre et al. | |
| 5,971,767 A | 10/1999 | Kaufman et al. | |
| 5,987,960 A | 11/1999 | Messner et al. | |
| 6,019,725 A | 2/2000 | Vesely et al. | |
| 6,047,080 A | 4/2000 | Chen et al. | |
| 6,083,162 A | 7/2000 | Vining | |
| 6,138,045 A | 10/2000 | Kupinski et al. | |
| 6,151,404 A | 11/2000 | Pieper | |
| 6,167,296 A | 12/2000 | Shahidi | |
| 6,181,348 B1 | 1/2001 | Geiger | |
| 6,201,387 B1 | 3/2001 | Govari | |
| 6,233,476 B1 | 5/2001 | Strommer et al. | |
| 6,246,784 B1 | 6/2001 | Summers et al. | |
| 6,266,551 B1 | 7/2001 | Osadchy et al. | |
| 6,332,089 B1 | 12/2001 | Acker et al. | |
| 6,346,940 B1 | 2/2002 | Fukunaga | |
| 6,366,800 B1 | 4/2002 | Vining et al. | |
| 6,381,485 B1 | 4/2002 | Hunter et al. | |
| 6,387,092 B1 | 5/2002 | Burnside et al. | |
| 6,466,815 B1 | 10/2002 | Saito et al. | |
| 6,496,188 B1 | 12/2002 | Deschamps et al. | |
| 6,501,848 B1 | 12/2002 | Carroll et al. | |
| 6,501,981 B1 | 12/2002 | Schweikard et al. | |
| 6,505,065 B1 | 1/2003 | Yanof et al. | |
| 6,522,907 B1 | 2/2003 | Bladen et al. | |
| 6,526,162 B2 | 2/2003 | Asano et al. | |
| 6,535,756 B1 | 3/2003 | Simon et al. | |
| 6,578,579 B2 | 6/2003 | Burnside et al. | |
| 6,584,174 B2 | 6/2003 | Schubert et al. | |
| 6,603,868 B1 | 8/2003 | Ludwig et al. | |
| 6,611,793 B1 | 8/2003 | Burnside et al. | |
| 6,650,927 B1 | 11/2003 | Keidar | |
| 6,651,669 B1 | 11/2003 | Burnside | |
| 6,694,163 B1 | 2/2004 | Vining | |
| 6,757,557 B1 | 6/2004 | Bladen et al. | |
| 6,783,523 B2 | 8/2004 | Qin et al. | |
| 6,792,390 B1 | 9/2004 | Burnside et al. | |
| 6,829,379 B1 | 12/2004 | Knoplioch et al. | |
| 6,850,794 B2 | 2/2005 | Shahidi | |
| 6,892,090 B2 | 5/2005 | Verard et al. | |
| 6,898,263 B2 | 5/2005 | Avinash et al. | |
| 6,909,913 B2 | 6/2005 | Vining | |
| 6,920,347 B2 | 7/2005 | Simon et al. | |
| 6,925,200 B2 | 8/2005 | Wood et al. | |
| 7,006,677 B2 | 2/2006 | Manjeshwar et al. | |
| 7,072,501 B2 | 7/2006 | Wood et al. | |
| 7,085,400 B1 | 8/2006 | Holsing et al. | |
| 7,096,148 B2 | 8/2006 | Anderson et al. | |
| 7,149,564 B2 | 12/2006 | Vining et al. | |
| 7,167,180 B1 | 1/2007 | Shibolet | |
| 7,174,202 B2 | 2/2007 | Bladen et al. | |
| 7,179,220 B2 * | 2/2007 | Kukuk | A61B 1/00147 600/101 |
| 7,206,462 B1 * | 4/2007 | Betke | G06T 7/0012 378/21 |
| 7,236,558 B2 | 6/2007 | Saito et al. | |
| 7,301,332 B2 | 11/2007 | Govari et al. | |
| 7,315,639 B2 | 1/2008 | Kuhnigk | |
| 7,324,104 B1 | 1/2008 | Bitter et al. | |
| 7,336,809 B2 | 2/2008 | Zeng et al. | |
| 7,397,937 B2 | 7/2008 | Schneider et al. | |
| 7,428,334 B2 | 9/2008 | Schoisswohl et al. | |
| 7,452,357 B2 | 11/2008 | Vlegele et al. | |
| 7,505,809 B2 | 3/2009 | Strommer et al. | |
| 7,517,320 B2 | 4/2009 | Wibowo et al. | |
| 7,518,619 B2 | 4/2009 | Stoval, III et al. | |
| 7,630,752 B2 | 12/2009 | Viswanathan | |
| 7,630,753 B2 | 12/2009 | Simon et al. | |
| 7,659,912 B2 | 2/2010 | Akimoto et al. | |
| 7,702,153 B2 | 4/2010 | Hong et al. | |
| 7,751,865 B2 | 7/2010 | Jascob et al. | |
| 7,756,316 B2 | 7/2010 | Odry et al. | |
| 7,788,060 B2 | 8/2010 | Schneider | |
| 7,792,565 B2 | 9/2010 | Vining | |
| 7,805,269 B2 | 9/2010 | Glossop | |
| 7,809,176 B2 | 10/2010 | Gundel | |
| 7,811,294 B2 | 10/2010 | Strommer et al. | |
| 7,822,461 B2 | 10/2010 | Geiger et al. | |
| 7,901,348 B2 * | 3/2011 | Soper | A61B 1/0008 600/117 |
| 7,907,772 B2 | 3/2011 | Wang et al. | |
| 7,929,014 B2 | 4/2011 | Akimoto et al. | |
| 7,951,070 B2 | 5/2011 | Ozaki et al. | |
| 7,969,142 B2 | 6/2011 | Krueger et al. | |
| 7,985,187 B2 | 7/2011 | Wibowo et al. | |
| 8,009,891 B2 | 8/2011 | de Vaan | |
| 8,049,777 B2 | 11/2011 | Akimoto et al. | |
| 8,055,323 B2 | 11/2011 | Sawyer | |
| 8,102,416 B2 | 1/2012 | Ito et al. | |
| 8,126,241 B2 | 2/2012 | Zarkh et al. | |
| 8,131,344 B2 | 3/2012 | Strommer et al. | |
| 8,170,328 B2 | 5/2012 | Masumoto et al. | |
| 8,199,981 B2 | 6/2012 | Koptenko et al. | |
| 8,200,314 B2 | 6/2012 | Bladen et al. | |
| 8,202,213 B2 | 6/2012 | Ito et al. | |
| 8,208,708 B2 | 6/2012 | Homan et al. | |
| 8,219,179 B2 | 7/2012 | Ganatra et al. | |
| 8,257,346 B2 | 9/2012 | Qin et al. | |
| 8,267,927 B2 | 9/2012 | Dalal et al. | |
| 8,290,228 B2 | 10/2012 | Cohen et al. | |
| 8,298,135 B2 | 10/2012 | Ito et al. | |
| 8,391,952 B2 | 3/2013 | Anderson | |
| 8,417,009 B2 | 4/2013 | Mizuno | |
| 8,494,612 B2 | 7/2013 | Vetter et al. | |
| 8,509,877 B2 | 8/2013 | Mori et al. | |
| 8,672,836 B2 | 3/2014 | Higgins et al. | |
| 8,682,045 B2 | 3/2014 | Vining et al. | |
| 8,696,549 B2 | 4/2014 | Holsing et al. | |
| 8,698,806 B2 | 4/2014 | Kunert et al. | |
| 8,700,132 B2 | 4/2014 | Ganatra et al. | |
| 8,706,193 B2 | 4/2014 | Govari et al. | |
| 8,709,034 B2 | 4/2014 | Keast et al. | |
| 8,730,237 B2 | 5/2014 | Ruijters et al. | |
| 8,768,029 B2 | 7/2014 | Helm et al. | |
| 8,784,400 B2 | 7/2014 | Roschak | |
| 8,798,227 B2 | 8/2014 | Tsukagoshi et al. | |
| 8,798,339 B2 | 8/2014 | Mielekamp et al. | |
| 8,801,601 B2 | 8/2014 | Prisco et al. | |
| 8,819,591 B2 | 8/2014 | Wang et al. | |
| 8,862,204 B2 | 10/2014 | Sobe et al. | |
| 9,754,367 B2 | 9/2017 | Lachmanovich et al. | |
| 10,062,166 B2 | 8/2018 | Lachmanovich et al. | |

(56) References Cited

U.S. PATENT DOCUMENTS

| | | | |
|---|---|---|---|
| 2005/0036668 A1* | 2/2005 | McLennan | G06K 9/4652 382/128 |
| 2005/0207630 A1* | 9/2005 | Chan | A61B 6/466 382/131 |
| 2007/0071301 A1* | 3/2007 | Kiraly | G06T 7/11 382/131 |
| 2008/0025584 A1* | 1/2008 | Kunz | G06K 9/4638 382/128 |
| 2008/0063136 A1* | 3/2008 | Ohyu | A61B 6/488 378/4 |
| 2008/0118135 A1* | 5/2008 | Averbuch | G06T 7/0012 382/131 |
| 2008/0183073 A1 | 7/2008 | Higgins et al. | |
| 2009/0012390 A1 | 1/2009 | Pescatore et al. | |
| 2009/0030306 A1 | 1/2009 | Miyoshi et al. | |
| 2009/0034813 A1* | 2/2009 | Dikmen | G06T 7/74 382/131 |
| 2009/0034816 A1* | 2/2009 | Ghanem | G06T 7/0012 382/131 |
| 2009/0185731 A1* | 7/2009 | Ray | G06T 7/0012 382/131 |
| 2010/0266172 A1* | 10/2010 | Shlomi | G09B 23/285 382/128 |
| 2010/0310146 A1* | 12/2010 | Higgins | G06F 19/00 382/131 |
| 2010/0312094 A1 | 12/2010 | Guttman et al. | |
| 2011/0158487 A1* | 6/2011 | Ohyu | A61B 6/463 382/128 |
| 2011/0237897 A1 | 9/2011 | Gilboa | |
| 2011/0251607 A1 | 10/2011 | Kruecker et al. | |
| 2012/0081362 A1 | 4/2012 | Kiraly et al. | |
| 2012/0099776 A1 | 4/2012 | Maeda et al. | |
| 2012/0203065 A1* | 8/2012 | Higgins | A61B 1/2676 600/109 |
| 2012/0249546 A1* | 10/2012 | Tschirren | G06T 19/00 345/419 |
| 2012/0280135 A1 | 11/2012 | Bal | |
| 2012/0287238 A1 | 11/2012 | Onishi et al. | |
| 2012/0288173 A1* | 11/2012 | Rai | G06K 9/46 382/131 |
| 2013/0165854 A1 | 6/2013 | Sandhu et al. | |
| 2013/0223702 A1* | 8/2013 | Holsing | A61B 5/113 382/128 |
| 2016/0005224 A1* | 1/2016 | Greenburg | G06T 11/008 345/419 |
| 2016/0371883 A1* | 12/2016 | Merkine | A61B 1/2676 |
| 2018/0220883 A1* | 8/2018 | Higgins | A61B 1/00009 |

OTHER PUBLICATIONS

Notice of Allowance issued in corresponding Japanese Appl. No. JP 2016-563463, dated Mar. 19, 2019, together with English language translation (5 pages).

Extended European Search Report for application No. 15815409.6 dated Dec. 15, 2017 (10 pages).

Seijo et al., "Preliminary Experience with the Use of Electromagnetic Navigation for the Diagnosis of Peripheral Pulmonary Nodules and Enlarged Mediastinal Lymph Nodes", Archivos De Bronconeumologia, Ediciones Doyma S.A., Barcelona, ES, vol. 43, No. 8, Jan. 2007, pp. 460-463.

Weiser et al., "Electromagnetic Navigational Bronchoscopy: A Surgeon's Perspective", The Annuals of Thoracic Surgery, Elsevier, Inc. United States., vol. 85, No. 2, Jan. 24, 2008, pp. S797-S801.

Klein et al., "Fiducial-Free Registration Procedure for Navigated Bronchoscopy", Medical Image Computing and Computer-Assisted Intervention—Miccai 2007; [Lecture Notes in Computer Science], Oct. 29, 2007 pp. 475-482.

Japanese Office Action issued in Appl. No. JP 2016-563463, dated Oct. 26, 2018, together with English language translation (11 pages).

Australian Examination Report issued in corresponding Appl. No. AU 2015284213 dated Mar. 8, 2019 (3 pages).

* cited by examiner

TRACHEA MARKING

CROSS REFERENCE TO RELATED APPLICATIONS

The present application is a continuation of U.S. patent application Ser. No. 15/682,893, filed on Aug. 22, 2017, which is a continuation of U.S. patent application Ser. No. 14/753,674, now U.S. Pat. No. 9,754,367, filed on Jun. 29, 2015, which claims the benefit of a priority to U.S. Provisional Patent Application Ser. No. 62/020,253 filed on Jul. 2, 2014, the entire contents of which are incorporated herein by reference.

BACKGROUND

Technical Field

The present disclosure relates to the treatment of patients with lung diseases and, more particularly, to devices, systems, and methods for marking the trachea in a three-dimensional (3D) model generated based on CT scan image data of a patient's lungs.

Discussion of Related Art

Visualization techniques related to visualizing a patient's lungs have been developed so as to help clinicians perform diagnoses and/or surgeries on the patient's lungs. Visualization is especially important for identifying a location of a diseased region. Further, when treating the diseased region, additional emphasis is given to identification of the particular location of the diseased region so that a surgical operation is performed at the correct location.

In the past, scanned two-dimensional images of the lungs have been used to aid in visualization. In order to visualize a lung from scanned two-dimensional images, it is important to determine whether or not an area of the two-dimensional images is a part of the lung. Thus, detecting a starting location where a navigation procedure will begin, for example, a location of an organ or other part that is connected to or is a part of the lung, is also important for identifying the lung. In one example, the trachea can be used as the starting location because the trachea has a substantially constant diameter along its length and is known to be connected to the lung.

SUMMARY

Provided in accordance with the present disclosure is a method of marking a main carina and a trachea of a patient.

According to an aspect of the present disclosure, the method includes importing, into an image processing computer, slice images of a chest of the patient from an imaging device, generating, by a graphics processor included in the image processing computer, a three-dimensional (3D) model based on the imported slice images, displaying, by the image processing computer, the 3D model in a graphical user interface (GUI), locating, by a user using the GUI, the main carina by viewing 2D images of the 3D model in an axial orientation, marking the main carina in one of the 2D images of the 3D model, adjusting a view plane of the 3D model around a rotation axis defined by the marked location of the main carina to adjust the view plane from an axial orientation to a coronal orientation while keeping the main carina in the view plane to thereby display the entire trachea on the GUI, and marking an upper end of the trachea in one of the 2D images of the 3D model.

According to another aspect of the present disclosure, the method includes importing, into an image processing computer, slice images of a chest of the patient from an imaging device, generating, by a graphics processor included in the image processing computer, a three-dimensional (3D) model based on the imported slice images, displaying, by the image processing computer, the 3D model in a graphical user interface (GUI), marking, by a user using the GUI, the main carina in one of a plurality of 2D images of the 3D model, adjusting, by the user using the GUI, a view plane of the 3D model to display the entire trachea on the GUI, and marking, by a user using the GUI, an upper end of the trachea in one of the plurality of 2D images of the 3D model.

In a further aspect of the present disclosure, the method further includes, prior to marking the main carina, locating the main carina in one of the 2D images of the 3D model.

In another aspect of the present disclosure, the user locates the main carina by viewing the 2D images of the 3D model in an axial orientation In yet another aspect of the present disclosure, the 3D model is generated based on two dimensional images obtained by tomographic technique, radiography, tomogram produced by a computerized axial tomography scan, magnetic resonance imaging, ultrasonography, contrast imaging, fluoroscopy, nuclear scans, or positron emission tomography.

In a further aspect of the present disclosure, adjusting a view plane of the 3D model includes adjusting the view plane around a rotation axis.

In another aspect of the present disclosure, adjusting the view plane around the rotation axis includes adjusting the view plane from an axial orientation to a coronal orientation.

In a further aspect of the present disclosure, during the adjusting, the main carina is kept within the view plane.

In another aspect of the present disclosure, the method further includes verifying, by the user using the GUI, the marking of the trachea by reviewing a rendering of the 3D model displayed on the GUI.

In a further aspect of the present disclosure, the rendered 3D model includes the marking of the main carina and the marking of the upper end of the trachea.

Any of the above aspects and embodiments of the present disclosure may be combined without departing from the scope of the present disclosure.

BRIEF DESCRIPTION OF THE DRAWINGS

Various aspects and features of the present disclosure are described herein below with references to the drawings, wherein.

DETAILED DESCRIPTION

Figure 1:
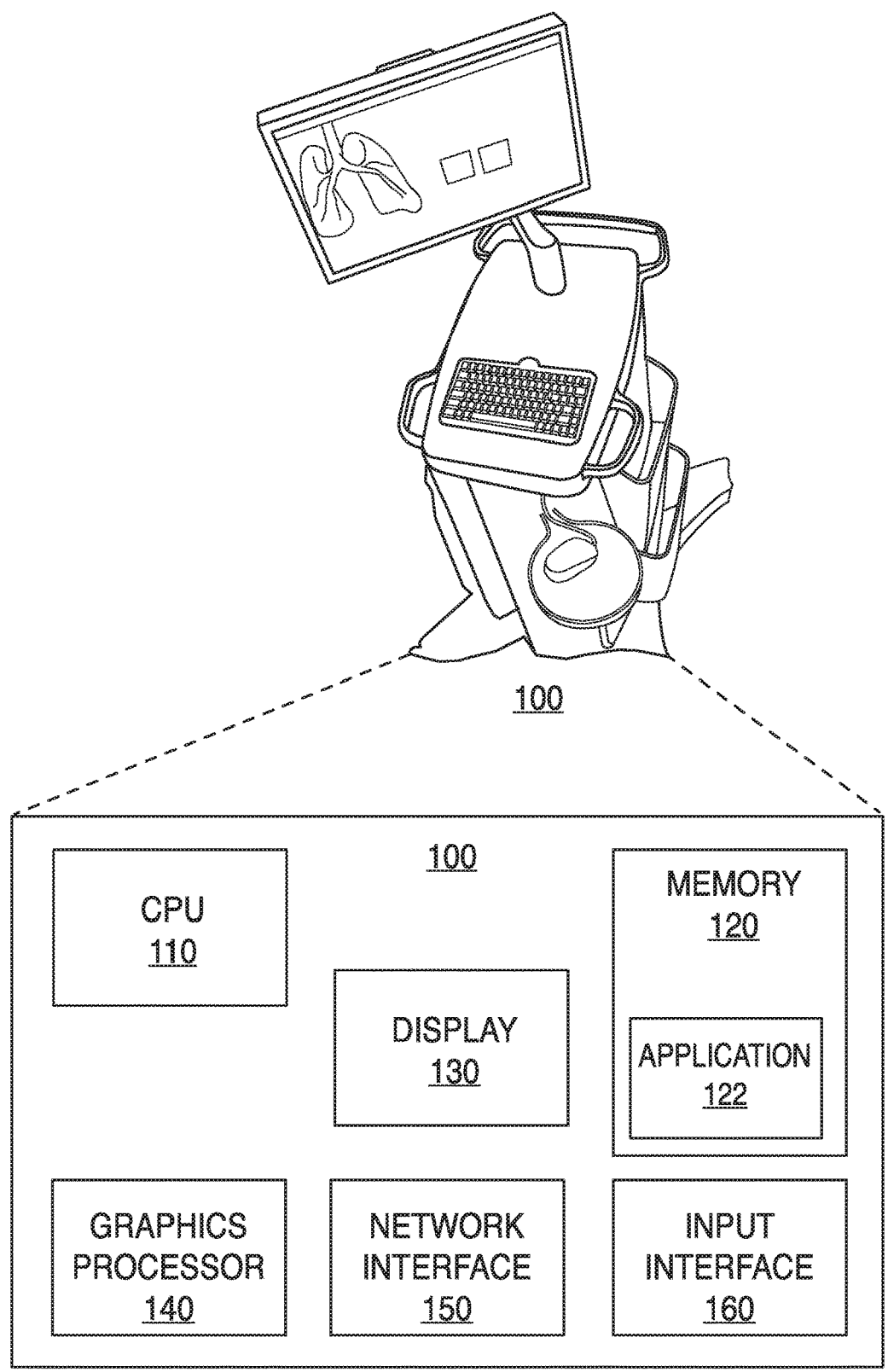
FIG. 1 is a schematic diagram of an example device which may be used to mark a trachea in a 3D model of a patient's lungs, in accordance with an embodiment of the present disclosure.

The present disclosure is related to devices, systems, and methods for identifying and manually marking a trachea and main carina on slice images of a patient's lungs when automatic detection of the trachea fails. Identifying the trachea may be a necessary component of pathway planning for performing an ELECTROMAGNETIC NAVIGATION BRONCHOSCOPY® (ENB) procedure using an electromagnetic navigation (EMN) system.

An ENB procedure generally involves at least two phases: (1) planning a pathway to a target located within, or adjacent to, the patient's lungs; and (2) navigating a probe to the target along the planned pathway. These phases are generally referred to as (1) "planning" and (2) "navigation." Prior to the planning phase, the patient's lungs are imaged by, for example, a computed tomography (CT) scan, although additional applicable methods of imaging will be known to those skilled in the art. The image data assembled during the CT scan may then be stored in, for example, the Digital Imaging and Communications in Medicine (DICOM) format, although additional applicable formats will be known to those skilled in the art. The CT scan image data may then be loaded into a planning software application ("application") to be processed for generating a 3D model which may be used during the planning phase of the ENB procedure.

The application may use the CT scan image data to generate a 3D model of the patient's lungs. The 3D model may include, among other things, a model airway tree corresponding to the actual airways of the patient's lungs, and showing the various passages, branches, and bifurcations of the patient's actual airway tree. While the CT scan image data may have gaps, omissions, and/or other imperfections included in the image data, the 3D model is a smooth representation of the patient's airways, with any such gaps, omissions, and/or imperfections in the CT scan image data filled in or corrected. As described in more detail below, the 3D model may be viewed in various orientations. For example, if a clinician desires to view a particular section of the patient's airways, the clinician may view the 3D model represented in a 3D rendering and rotate and/or zoom in on the particular section of the patient's airways. Additionally, the clinician may view the 3D model represented in two-dimensional (2D) slice images generated along the axial, sagittal, and coronal planes, and may "scroll through" such 2D slice images to a "depth" showing the particular section of the patient's airways. The planning phase generally involves identifying at least one target nodule in the 3D model, and generating a pathway to the target. The pathway will generally run from the patient's mouth, through the trachea and connected airways, to the target. However, in order to generate the pathway to the target, the location of the trachea within the 3D model must be known. Generally, the application will automatically detect the trachea within the 3D model. This process is more fully described in commonly-owned U.S. Provisional Patent Application Ser. No. 62/020,257 entitled "Automatic Detection of Human Lung Trachea", filed on Jul. 2, 2014, by Markov et al., the entire contents of which are hereby incorporated by reference. However, there may be instances where automatic detection of the trachea fails. The present disclosure is directed to devices, systems, and methods for manually marking the trachea in such instances.

The trachea provides a passage way for breathing. The trachea is connected to the larynx and the pharynx in the upper end. In particular, the upper part of the trachea extends substantially linearly from the larynx and pharynx and behind the sternum. The lower end of the trachea branches into a pair of smaller tubes, i.e., primary bronchi, each tube connecting to a lung. The main carina is a cartilaginous ridge formed by the branching of the trachea into the primary bronchi. The diameter of the trachea is substantially constant along its length (i.e., the axial direction), while the size of the lung changes substantially along the same direction as the length of the trachea. Thus, by analyzing 2D slice images of the 3D model, the trachea may be detected. For this reason, images generated along the axial plane may be analyzed to detect the trachea in the present disclosure. In other embodiments, images generated along other planes may also be used to detect the trachea.

FIG. 1 shows an image processing device 100 that may be used during the planning phase of an ENB procedure to manually mark the location of the trachea in the 3D model. Device 100 may be a specialized image processing computer configured to perform the functions described below. Device 100 may be embodied in any form factor known to those skilled in the art, such as, a laptop, desktop, tablet, or other similar computer. Device 100 may include, among other things, one or more processors 110, memory 120 storing, among other things, the above-referenced application 122, a display 130, one or more specialized graphics processors 140, a network interface 150, and one or more input interfaces 160.

Figure 2:
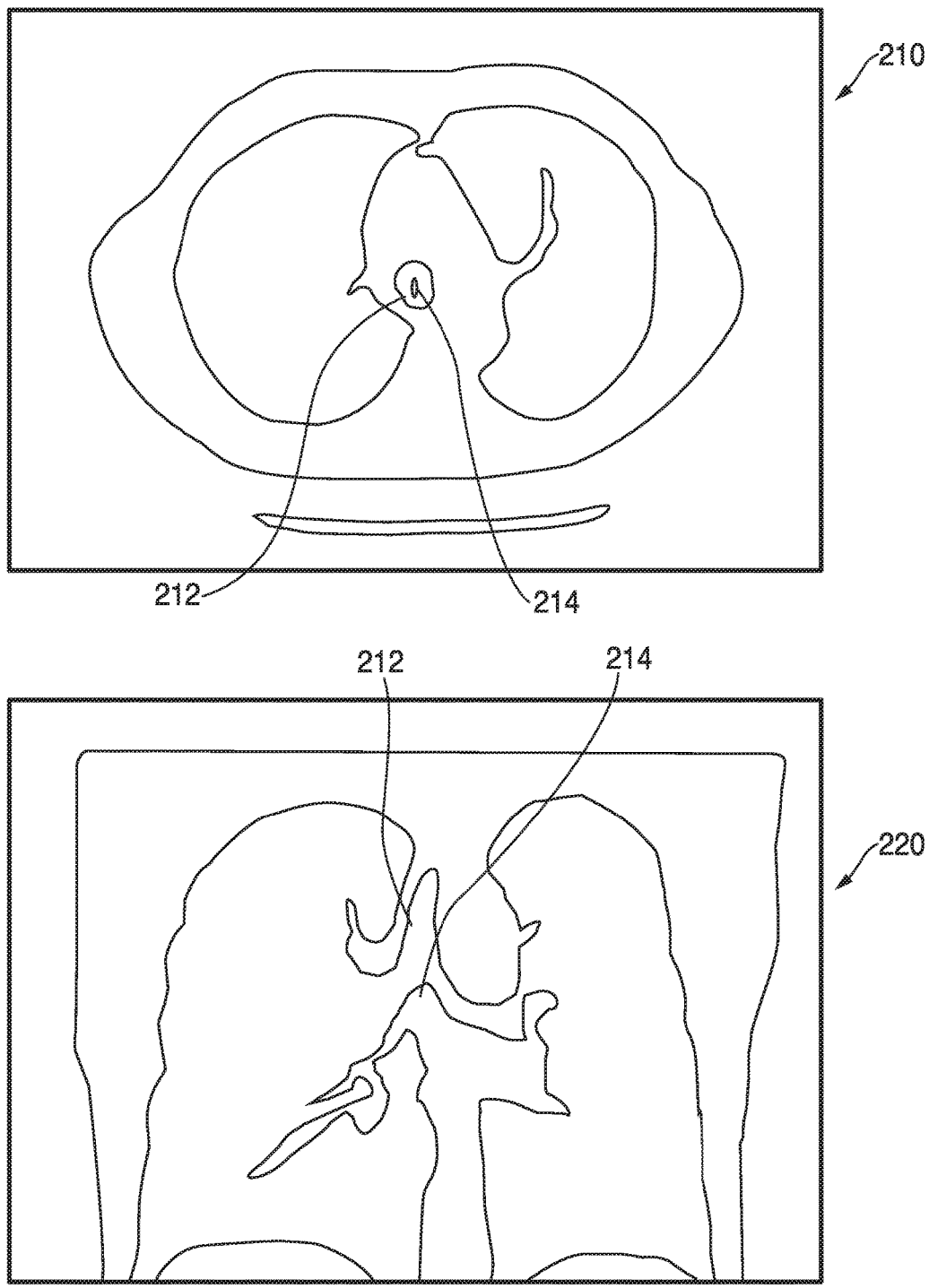
FIG. 2 depicts 2D slice images generated from the 3D model showing the trachea in the axial and coronal orientations, in accordance with embodiments of the present disclosure.

As noted above, 2D slice images of the 3D model may be displayed in various orientations. As an example, FIG. 2 shows 2D slice images of the 3D model of the patient's lungs in the axial and coronal orientations, with 2D slice image 210 generated along the axial plane and 2D slice image 220 generated along the coronal plane. Both 2D slice images 210 and 220 show the trachea 212 and the main carina 214.

The 2D slice images of the 3D model may show a high density area with high intensity and a low density area with low intensity. For example, bones, muscles, blood vessels, or cancerous portions are displayed with higher intensity than an inside area of airways of the lung. The 2D slice images of the 3D model may be further processed to obtain binarized 2D slice images, which only includes black and white pixels. The binarized 2D slice images may show white regions as non-lung areas (e.g., bones, stomach, heart, blood vessels, walls of airways, etc.) and black regions as lung areas (e.g., the lung, the trachea, and connected components).

Figure 3:
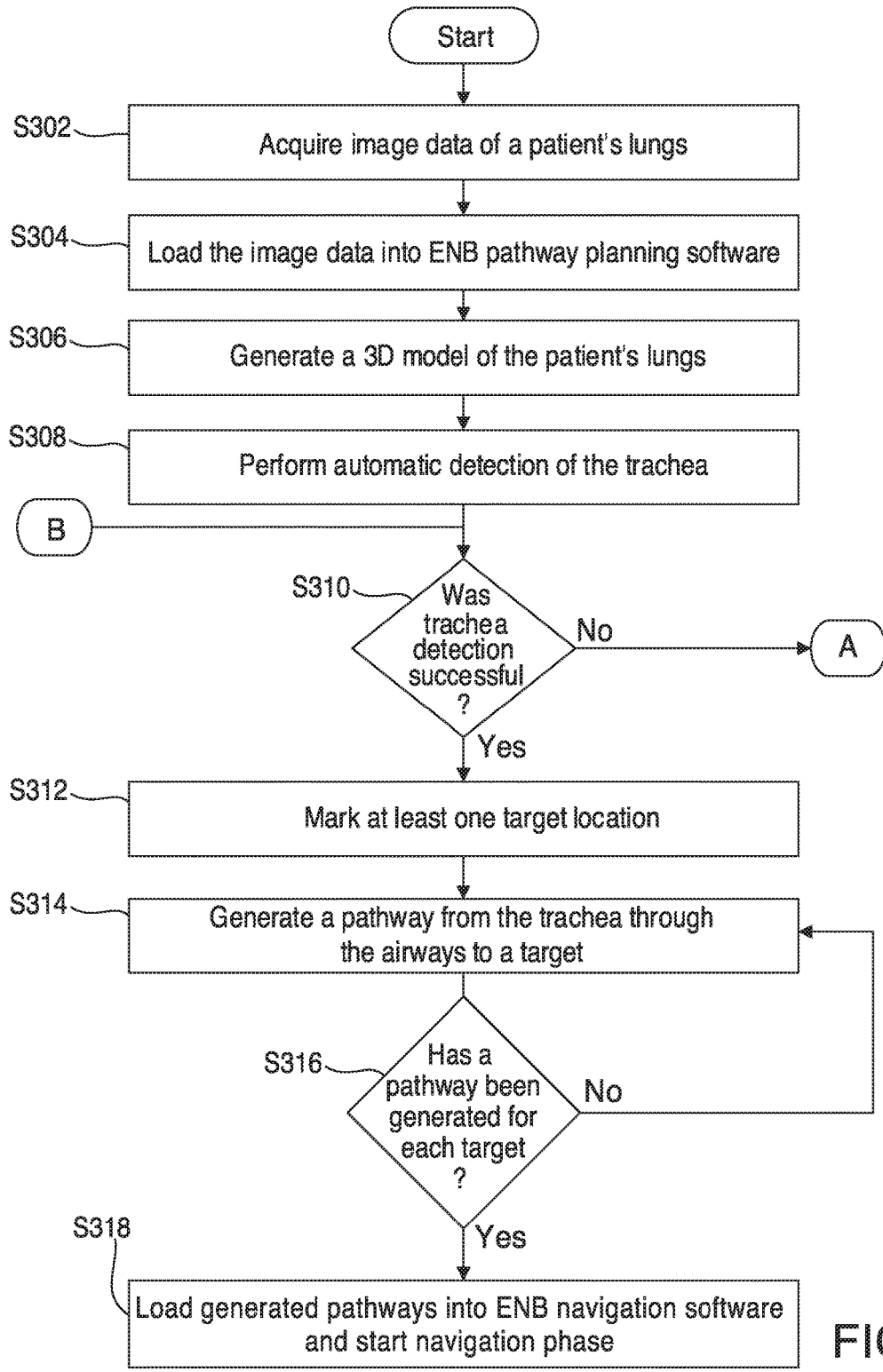
FIG. 3 is a flowchart illustrating an example method for performing an ENB procedure, in accordance with an embodiment of the present disclosure.

FIG. 3 is a flowchart illustrating an example method for performing the planning phase of an ENB procedure, in accordance with the present disclosure. Starting with step S302, image data of the patient's lungs are acquired. Image data may be acquired using any effective imaging modality, e.g., a CT scan, radiography such as an X-ray scan, tomogram produced by a computerized axial tomography (CAT) scan, magnetic resonance imaging (MRI), ultrasonography, contrast imaging, fluoroscopy, nuclear scans, and/or positron emission tomography (PET). Thereafter, at step S304, the acquired image data is loaded into ENB planning software. The ENB planning software then, at step S306, attempts to automatically detect the trachea from the image data. At step S308 it is determined whether the trachea detection was successful. If the trachea has not successfully been detected, manual detection is necessary. One method of manually detecting the trachea in accordance with the present disclosure is detailed below with reference to FIG. 4.

When the trachea has successfully been detected, the ENB planning software enables a clinician, at step S310, to mark one or more target locations in the image data. Thereafter, at step S312, the ENB software generates a pathway from the trachea through the patient's airways to the target. At step S314 it is determined whether a pathway has been generated for each target marked by the clinician. If not, processing returns to step S312. If yes, the planning phase of the ENB procedure is complete, and, at step S316, the generated pathways may be loaded into ENB navigation software to start the navigation phase of the ENB procedure, or stored for later use.

Figure 4:
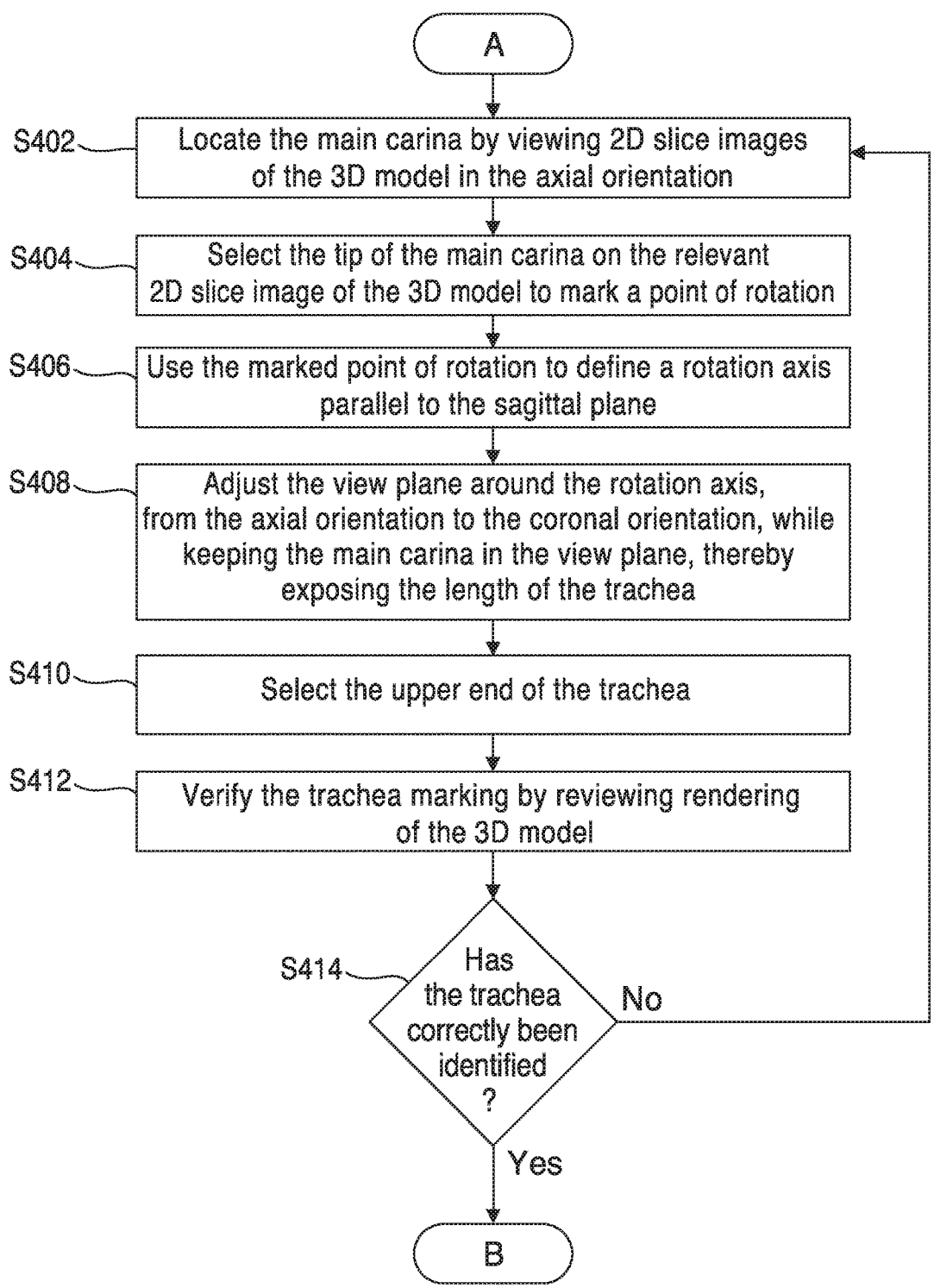
FIG. 4 is a flowchart illustrating an example method for manually marking a trachea in a 3D model of a patient's lungs, in accordance with an embodiment of the present disclosure.
Figure 5:
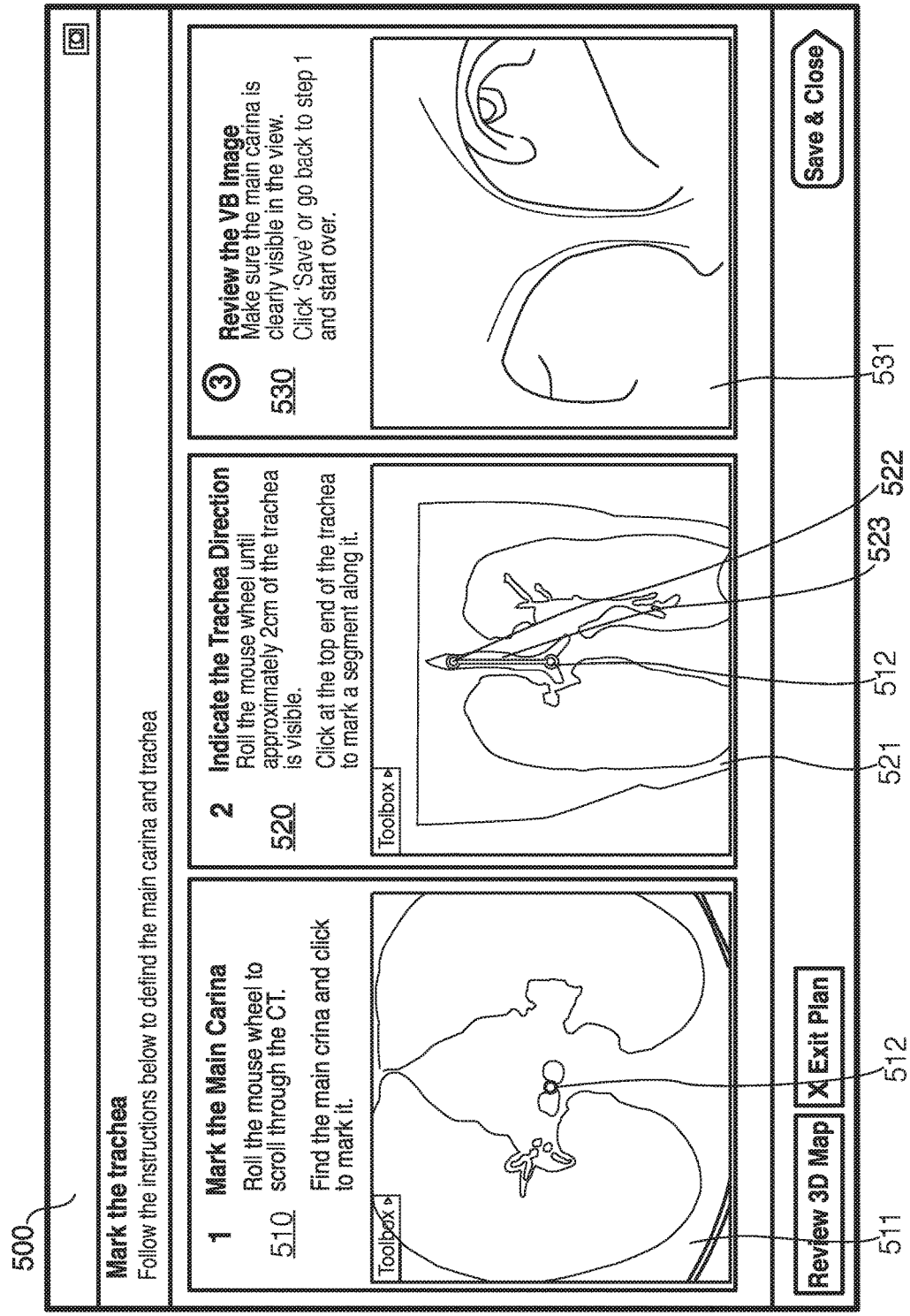
FIG. 5 is an example view which may be presented by electromagnetic navigation pathway planning software to enable a clinician to manually mark a trachea in a 3D model of a patient's lungs, in accordance with an embodiment of the present disclosure.

FIG. 4 is a flowchart of an example method for manually marking the trachea in the 3D model by using an example view of application 122 shown in FIG. 5. This example method will be processed if it is determined, at step S308 of FIG. 3, that the trachea detection was unsuccessful. Application 122 may present various views of the 3D model to assist the clinician in marking the trachea. In an embodiment, the 2D slice images of the 3D model may be used. In other embodiments, other views of the 3D model may be used. Starting at step S402, a clinician may locate the main carina by viewing the 2D slice images of the 3D model in the axial orientation, as shown in subview 510 of FIG. 5. The clinician may have to view and "scroll through" multiple 2D slice images before finding the correct 2D slice image 511 showing the bifurcation of the trachea into the primary bronchi, and thus also the tip of the main carina.

Upon finding the 2D slice image showing the tip of the main carina, the clinician, at step S404, selects the tip of the main carina to mark a point of rotation 512. Then, at step S406, using the marked point of rotation 512, a rotation axis is defined passing through the point of rotation and parallel to the sagittal plane. Thereafter, at step S408, the clinician adjusts the view plane around the rotation axis, from an axial orientation to a coronal orientation, while keeping the main carina in the view plane, thereby exposing the length of the trachea 523, as shown in subview 520 of FIG. 5. Thus, the clinician adjusts the view plane from a 2D slice image generated along the axial plane, such as 2D slice image 210 shown in FIG. 2, to a 2D slice image generated along the coronal plane, such as 2D slice image 220 shown in FIG. 2. The clinician may again have to view and "scroll through" multiple 2D slice images before finding a 2D slice image 521 showing the length of the trachea 523.

Upon finding the 2D slice image showing the length of the trachea 523, the clinician, at step S410, selects the upper end of the trachea 523 to mark a second point 522. Subview 520 may then show the point of rotation 512 and the second point, respectively marking the lower and upper ends of the trachea 523. Thereafter, the clinician may verify that the trachea 523 has been correctly identified by viewing a rendering 531 of the 3D model of the patient's airways looking down the trachea 523 from the second point 522 towards the main carina, as shown by subview 530 of FIG. 5. If, upon verification, the clinician determines at step S414 that the trachea 523 has not been correctly identified, processing returns to step S402. If the clinician determines that the trachea 523 has been correctly identified, processing returns to step S308 of FIG. 3 and completes the planning phase of the ENB procedure.

Returning now to FIG. 1, memory 120 includes application 122 such as EMN planning and procedure software and other data that may be executed by processors 110. For example, the data may be the CT scan image data stored in the DICOM format and/or the 3D model generated based on the CT scan image data. Memory 120 may also store other related data, such as medical records of the patient, prescriptions and/or a disease history of the patient. Memory 120 may be one or more solid-state storage devices, flash memory chips, mass storages, tape drives, or any computer-readable storage media which are connected to a processor through a storage controller and a communications bus. Computer readable storage media include non-transitory, volatile and non-volatile, removable and non-removable media implemented in any method or technology for storage of information such as computer-readable instructions, data structures, program modules or other data. For example, computer-readable storage media includes random access memory (RAM), read-only memory (ROM), erasable programmable read only memory (EPROM), electrically erasable programmable read only memory (EEPROM), flash memory or other solid state memory technology, CD-ROM, DVD or other optical storage, magnetic cassettes, magnetic tape, magnetic disk storage or other magnetic storage devices, or any other medium which can be used to store desired information and which can be accessed by device 100.

Display 130 may be touch-sensitive and/or voice-activated, enabling display 130 to serve as both an input device and an output device. Graphics processors 140 may be specialized graphics processors which perform image-processing functions, such as processing the CT scan image data to generate the 3D model, and process the 3D model to generate the 2D slice images of the 3D model in the various orientations as described above, as well as the 3D renderings of the 3D model. Graphics processors 140 may further be configured to generate a graphical user interface (GUI) to be displayed on display 130. The GUI may include views showing the 2D image slices, the 3D rendering, among other things. In embodiments, graphics processors 140 may be specialized graphics processors, such as a dedicated graphics processing unit (GPU), which performs only the image processing functions so that the one or more general processors 110 may be available for other functions. The specialized GPU may be a stand-alone dedicated graphics card, or an integrated graphics card.

Network interface 150 enables device 100 to communicate with other devices through a wired and/or wireless network connection. In an embodiment, device 100 may receive the CT scan image data from an imaging device via a network connection. In other embodiments, device 100 may receive the CT scan image data via a storage device, such as a disk or other external storage media known to those skilled in the art.

Input interface 160 is used for inputting data or control information, such as setting values, text information, and/or controlling device 100. Input interface 160 may include a keyboard, mouse, touch sensor, camera, microphone, or other data input devices or sensors used for user interaction known to those skilled in the art.

Although the present disclosure has been described in terms of specific illustrative embodiments, it will be readily apparent to those skilled in this art that various modifications, rearrangements and substitutions may be made without departing from the spirit of the present disclosure. The scope of the present disclosure is defined by the claims appended hereto.

Further aspects of image and data generation, management, and manipulation useable in either the planning or navigation phases of an ENB procedure are more fully described in commonly-owned U.S. patent application Ser.

Nos. 13/838,805; 13/838,997; and Ser. No. 13/839,224, all entitled "Pathway Planning System and Method", filed on Mar. 15, 2013, by Baker, the entire contents of which are hereby incorporated by reference. Further aspects of the planning phase as well as the navigation phase of an ENB procedure are more fully described in commonly-owned U.S. Provisional Patent Application Ser. No. 62/020,220 entitled "Real-Time Automatic Registration Feedback", filed on Jul. 2, 2014, by Brown et al.; U.S. Provisional Patent Application Ser. No. 62/020,177 entitled "Methods for Marking Biopsy Location", filed on Jul. 2, 2014, by Brown.; U.S. Provisional Patent Application Ser. No. 62/020,240 entitled "System and Method for Navigating Within the Lung", filed on Jul. 2, 2014, by Brown et al.; U.S. Provisional Patent Application Ser. No. 62/020,238 entitled "Intelligent Display", filed on Jul. 2, 2014, by Kehat et al.; U.S. Provisional Patent Application Ser. No. 62/020,242 entitled "Unified Coordinate System for Multiple CT Scans of Patient Lungs", filed on Jul. 2, 2014, by Greenburg.; U.S. Provisional Patent Application Ser. No. 62/020,245 entitled "Alignment CT", filed on Jul. 2, 2014, by Klein et al.; U.S. Provisional Patent Application Ser. No. 62/020,250 entitled "Algorithm for Fluoroscopic Pose Estimation", filed on Jul. 2, 2014, by Merlet.; U.S. Provisional Patent Application Ser. No. 62/020,261 entitled "System and Method for Segmentation of Lung", filed on Jul. 2, 2014, by Markov et al.; U.S. Provisional Patent Application Ser. No. 62/020,258 entitled "Cone View—A Method of Providing Distance and Orientation Feedback While Navigating in 3D", filed on Jul. 2, 2014, by Lachmanovich et al.; and U.S. Provisional Patent Application Ser. No. 62/020,262 entitled "Dynamic 3D Lung Map View for Tool Navigation Inside the Lung", filed on Jul. 2, 2014, by Weingarten et al., the entire contents of all of which are hereby incorporated by reference.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A non-transitory computer-readable storage medium storing instructions for marking a trachea of a patient, the instructions, when executed by a processor, cause a computing device to:
generate a three-dimensional (3D) model based on a plurality of two-dimensional (2D) images of the patient;
receive, via a graphical user interface (GUI), a first mark at a main carina in one of the plurality of two-dimensional (2D) images of the patient;
adjust a view plane of the three-dimensional (3D) model around a rotation axis defined by the first mark; and
receive, via the GUI, a second mark at an upper end of the trachea in one of the plurality of 2D images of the patient.

2. The non-transitory computer-readable storage medium according to claim 1, wherein the rotation axis is parallel to a sagittal plane.

3. The non-transitory computer-readable storage medium according to claim 1, wherein adjusting of the view plane of the 3D model around the rotation axis is from an axial orientation to a coronal orientation while keeping the main carina in the view plane.

4. The non-transitory computer-readable storage medium according to claim 3, wherein adjusting of the view plane of the 3D model to the coronal orientation while keeping the main carina in the view plane causes the trachea to be displayed on the GUI.

5. The non-transitory computer-readable storage medium according to claim 3, wherein the instructions, when executed by the processor, further cause the computing device to, prior to receiving the first mark at the main carina, locate the main carina in one of the plurality of 2D images of the patient.

6. The non-transitory computer-readable storage medium according to claim 5, wherein the main carina is located based on input received from a user viewing the plurality of 2D images of the patient in the axial orientation.

7. The non-transitory computer-readable storage medium according to claim 1, wherein the plurality of 2D images are obtained by computed tomography, radiography, tomogram produced by a computerized axial tomography scan, magnetic resonance imaging, ultrasonography, contrast imaging, fluoroscopy, nuclear scans, or positron emission tomography.

8. The non-transitory computer-readable storage medium according to claim 1, wherein the instructions, when executed by the processor, further cause the computing device to verify the first mark at the main carina and the second mark at the upper end of the trachea by reviewing a rendering of the 3D model displayed on the GUI.

9. The non-transitory computer-readable storage medium according to claim 8, wherein the rendered 3D model includes the first mark of the main carina and the second mark of the upper end of the trachea.

10. The non-transitory computer-readable storage medium according to claim 1, wherein the instructions, when executed by the processor, further cause the computing device to generate a pathway including the trachea to a target within the patient.

11. The non-transitory computer-readable storage medium according to claim 10, wherein the instructions, when executed by the processor, further cause the computing device to load the pathway including the trachea to the target into an electromagnetic navigation program.

12. A method for detecting a trachea of a patient, the method comprising:
generating a three-dimensional (3D) model based on a plurality of two-dimensional (2D) images of the patient;
receiving, via a graphical user interface (GUI), a first marking at a first portion of the trachea of the patient in one of a plurality of the 2D images;
adjusting a view plane of the 3D model around a rotation axis defined by the first marking while maintaining the first marking in the view plane;
receiving, via the GUI, a second marking at a second portion of the trachea in one of the plurality of 2D images while the 3D model is in the adjusted view plane; and
displaying, via the GUI, a rendering of the 3D model depicting a view within the trachea from the second marking towards the first marking.

* * * * *